United States Patent [19]
Wang et al.

[11] Patent Number: 5,542,286
[45] Date of Patent: Aug. 6, 1996

[54] METHOD AND APPARATUS FOR CORRECTING FLOW AND PRESSURE SENSOR DRIFT IN A GAS CHROMATOGRAPH

[75] Inventors: Tak K. Wang, Havertown; Robert C. Henderson, Avondale, both of Pa.

[73] Assignee: Hewlett-Packard Company, Palo Alto, Calif.

[21] Appl. No.: 376,718

[22] Filed: Jan. 23, 1995

[51] Int. Cl.$^6$ .................................................. G01N 30/38
[52] U.S. Cl. ................... 73/23.22; 73/23.24; 73/3
[58] Field of Search ............................ 73/3, 23.21, 23.22, 73/23.24

[56] References Cited

U.S. PATENT DOCUMENTS

| | | | |
|---|---|---|---|
| 2,875,606 | 3/1959 | Robinson | 73/23.24 |
| 3,446,057 | 5/1969 | Bakalyar et al. | 73/23.24 |
| 3,879,984 | 4/1975 | Welland | 73/23.24 |
| 4,379,402 | 4/1983 | Harman, III | 73/23.21 |
| 4,994,096 | 2/1991 | Klein et al. | 95/82 |
| 5,476,000 | 12/1995 | Henderson et al. | 73/23.24 |

FOREIGN PATENT DOCUMENTS

| | | | |
|---|---|---|---|
| 158264 | 12/1979 | Japan | 73/3 |
| 73251 | 3/1989 | Japan | 73/23.24 |
| 208818 | 7/1992 | Japan | 73/3 |

*Primary Examiner*—Hezron E. Williams
*Assistant Examiner*—Daniel S. Larkin
*Attorney, Agent, or Firm*—John L. Imperato; Jonathan B. Penn

[57] ABSTRACT

A method and apparatus for correcting flow and pressure sensor drift in a gas chromatograph. At a convenient time when the chromatograph is not being used for analysis, the input valves controlling the input into the chromatograph are shut, reducing internal flow to zero. The indicated rate of flow is then measured using the flow sensor. If the value measured by the flow sensor during this test is different than the originally calibrated offset by some predetermined amount, then the newly measured value replaces the stored offset value. In a chromatograph where some minimum internal gas or liquid flow is necessary to prevent contamination of the instrument, a three-way valve can direct liquid or gas flow away from the flow sensor during this calibration run without eliminating internal flow through the chromatograph. To calibrate the pressure sensor, the pressure sensor is vented to ambient air pressure and its reading at that pressure is then used as an offset during later sample analysis.

4 Claims, 3 Drawing Sheets

METHOD AND APPARATUS FOR CORRECTING FLOW AND PRESSURE SENSOR DRIFT IN A GAS CHROMATOGRAPH

BACKGROUND OF THE INVENTION

In analytical chemistry, liquid and gas chromatography techniques have become important tools in the identification of chemical sample components. The basic principle underlying all chromatographic techniques is the separation of a sample chemical mixture into individual components by transporting the mixture in moving fluid through a retentive media. The moving fluid is called the mobile phase and the retentive media is the stationary phase. One of the differences between liquid and gas chromatography is that the mobile phase is either a liquid or gas, respectively.

In a gas chromatograph ("GC"), a supply of inert carrier gas(mobile phase) is continually passed as a stream through a heated column containing porous media coated with the sorptive stationary phase. Alternatively, a GC column comprises a hollow capillary tube having an inner diameter of from 50 to several hundred microns. A sample of the subject mixture is injected into the mobile phase stream and passed through the column. As the subject mixture passes through the column, components of the sample adhere at differential rates to the wall of the capillary tube or the sorptive media. Separation is due primarily to differences in the adhesion characteristics of the sample's active components with respect to the column. A detector, positioned at the outlet end of the column, detects each of the separated components as it exits the column.

The analytical choice between liquid and gas chromatography techniques is largely dependent on the molecular weight of the components being analyzed. Liquid chromatography can analyze much heavier compounds than gas chromatography. However, gas chromatography detection techniques are more sensitive and therefore generally preferred.

The accuracy of any analysis performed by a GC is dependent upon an accurate knowledge of the amount of carrier gas and sample gas flowing into and through the GC. Systems having valves and flow sensors for measuring the flow rate of the carrier gas, the flow rate of the sample, and the pressure of both are known. One GC having such valves and sensors is described in U.S. Pat. No. 4,948,389.

Although the flow and pressure sensors can be calibrated, long term drift can degrade the accuracy of both these sensors over time. All attempts to reduce the sensitivity of the flow and pressure sensors to the effects of long term drift have been unsuccessful. The problem is almost certainly related to the basic process and materials used to fabricate the sensors. The problem of sensor degradation over time has not been solved in the known art.

SUMMARY OF THE INVENTION

The present invention comprises a method for adjusting for the effects of long term drift in flow and pressure sensors so that the accuracy of the GC's measurements is maintained. The method does not entail the addition of any apparatus to the GC and does not impact the user of the GC in any appreciable fashion.

At a convenient time, either before or after operation of the GC, or whenever the GC is in a known, non-running state, the inlet valve is shut for a period of several seconds. During this "off" time, the output of the flow sensor is measured. If the current offset value, which is initially the factory calibrated offset, is not exceeded by the newly measured offset value by a predetermined amount, the current offset value is kept. If the newly measured value does exceed the current offset value by the predetermined amount, the new measurement replaces the current offset value.

The pressure sensor is calibrated by isolating it from the flow of sample and carrier gas. The pressure sensor is then vented to ambient atmospheric pressure. Measuring the reading of the sensor in this condition generates an offset value.

These methods of recalibrating the flow and pressure sensors on an ongoing basis eliminate the effects of flow and pressure sensor degradation over time for users that are operating their GC at temperatures significantly different from the temperatures experienced by the GC during factory calibration. The method does not require new hardware and renders the GC essentially insensitive to shifts in the flow sensor.

The present invention will now be described in detail with reference to the figures listed.

DETAILED DESCRIPTION OF THE INVENTION

In a gas chromatographic analysis, an inert carrier gas is passed through a temperature-controlled column which contains a stationary phase in the form of porous sorptive media, or through a hollow capillary tube having an inner diameter in the range of fifty to a few hundred microns coated with the stationary phase. A sample of the subject mixture is injected into the carder gas stream and passed through the column. As the subject mixture passes through the column, it adheres more or less strongly to the column. Separation is due primarily to differences in the adhesion of each sample component in the mobile phase to the stationary phase. These differences are also a function of the temperature of the column. A detector, positioned at the outlet end of the column, detects each of the separated components contained in the carrier fluid as it exits the column.

Figure 1:
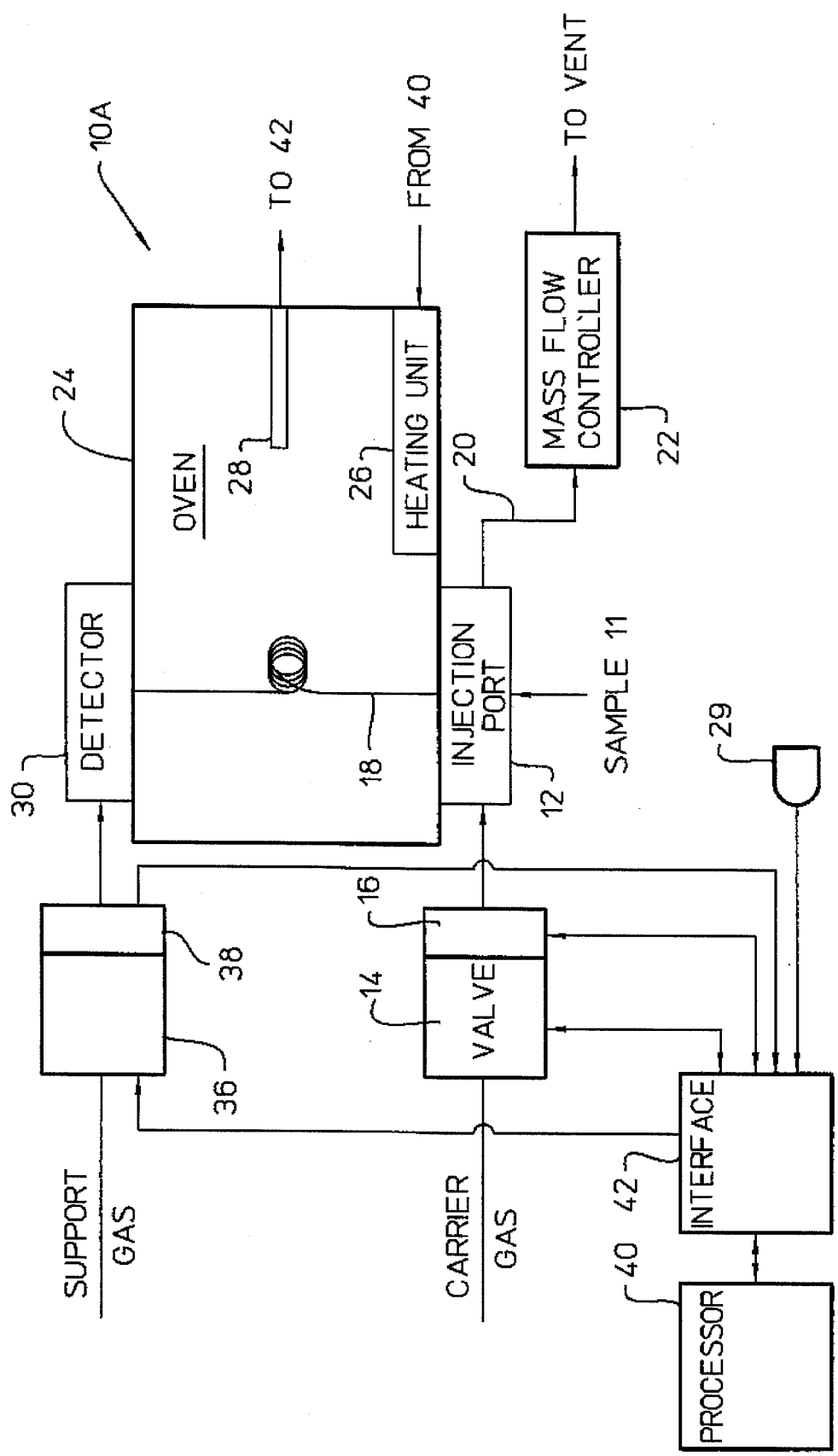
FIG. 1 is a simplified schematic representation of a preferred embodiment of a gas chromatograph analysis system constructed according to the teachings of the present invention.

The preferred embodiment shown in FIG. 1 is a gas chromatograph analytical system 10A arranged in a forward pressure regulated configuration, which is amenable for use with so-called cool on-column, packed, and large bore (i.e., about 530 micron) direct techniques. In order to perform a chromatographic separation of a given sample compound, a sample 11 is injected into a fluid by means of an injection port 12. The carrier gas is supplied to injection port 12 from a source through a fluid flow controller preferably in the form of valve 14. The operation of the flow controller serves to control the pressure and/or the volumetric flow rate of the carder gas in the GC system. The carrier gas may comprise one or more component gasses such as hydrogen, nitrogen, or helium, depending on the chromatographic separation being performed.

A plurality of transducers generate sense signals representative of actual operating conditions for use in the control system. Preferably, one sensed parameter is the inlet pressure of the carrier gas provided to injection port 12. This inlet pressure sense signal is provided by an inlet pressure sensor 16 to interface 42. The signal is then provided to processor 40, which in turn provides a control signal to valve 14. Operation of valve 14 then regulates the pressure of the carrier gas in response to the control signal. The particular designs of valve 14 and pressure sensor 16 are not critical herein and both are commercially available.

Injection port 12 provides a portion of the sample/carrier gas mixture to a separation column 18, with the remainder passing through a non-analyzed output 20. The flow exiting as non-analyzed output is known as the septum purge flow. By maintaining a relatively constant purge flow through a downstream-referenced flow controller 22, it is possible to minimize "false" peaks from the injection port septum(not shown) and also minimize air diffusion into column 18. Column 18 is positioned within a temperature-controlled thermal chamber or oven 24. Oven 24 preferably includes heating unit 26 and temperature sensor 28. In order to ensure that the temperature within oven 24 is at a desired level, temperature sensor 28 generates a temperature signal which is provided to interface 42 and processor 40. Heating unit 26 maintains controlled temperature in oven 24 in response to the control signal generated by processor 40. The carrier gas/sample combination passing through column 18 is thereby exposed to a temperature profile resulting from the operation of heater 26 within oven 24. Typically, the temperature in oven 24 is controlled according to a selected program so that sample 11 separates into its components.

As the carrier gas containing the sample exits column 18, the presence of one or more sample constituent components is detected by detector 30. Detector 30 can be any of the GC detectors known in the art, so long as it is capable of determining at least one physiochemical property of the carrier fluid which exits column 18. The term "detector" includes a wide variety of useful chromatographic detectors, such as flame ionization detectors, photoionization detectors, nitrogen phosphorous detectors, flame photometric detectors, thermal conductivity detectors, atomic emission detectors, electrolytic conductivity detectors, and electron capture detectors. Mass spectral detectors and infrared spectral detectors are also known.

Another transducer in the form of absolute ambient pressure sensor 29 provides a signal representative of the ambient barometric pressure at the outlet to interface 42 and processor 40. The sense signal may be considered for the purposes of the invention to also represent the column outlet pressure referenced to absolute pressure. A suitable absolute pressure transducer 29 may be constructed with a diaphragm mounted across a volume that contains a vacuum, whereby the transducer provides a signal representative of the pressure differential across the diaphragm.

The pressure of the carrier gas can also be regulated according to a back pressure mode, wherein valve 14 regulates pressure sensed in the region located upstream from the valve.

Depending upon the particular choice of detector 30, the preferred embodiments may also include means for providing support gas to the detector. The support gas may comprise one or more component gasses such as hydrogen, nitrogen, helium, air or oxygen, depending upon the detector employed. The pressure of the support gas entering detector 30 is sensed by transducer 38 to provide another signal representative of that operating condition parameter to interface 42 and processor 40. The pressure of the support gas is then controlled by valve 36 in response to an appropriate signal through interface 42 from the processor 40. Suitable support gas sources, valves, and transducers, along with related apparatus not shown, may be selected as known in the art.

Figure 2:
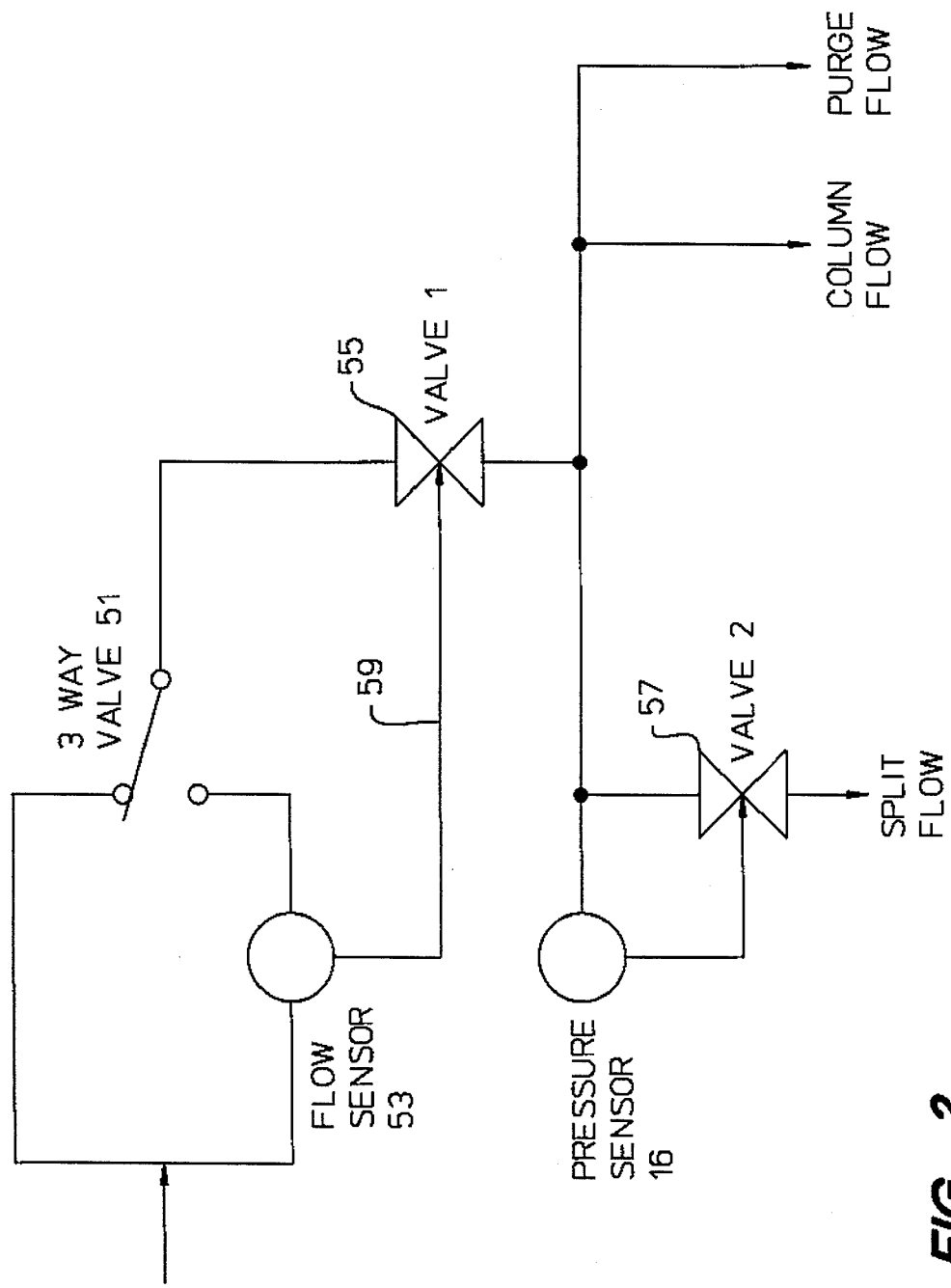
FIG. 2 illustrates a first embodiment of the input side of a GC embodying the present invention.

FIG. 2 shows further detail of input valve 14 and pressure sensor 16. As shown in FIG. 2, the input apparatus further comprises three way valve 51 and flow sensor 53. In this embodiment, input valve 14 is comprised of first and second input valves 55 and 57, respectively. Pressure sensor 16 is coupled to both first and second input valves 55 and 57. Electronic control line 59 couples flow sensor 53 and valve 55. By closing and opening three way valve 51, flow can be directed either through or away from flow sensor 53. Valve 51 can establish a no flow condition through the flow sensor while flow is maintained in the column and purge regulator.

In a Split/Splitless mode of operation, flow control is required only during injection of the sample when the total flow is used to establish the split ratio, which is the ratio of the total sample to the sample that actual goes through the sample column. In the splitless mode, valve 57 is shut. Valve 55 is under the control of pressure sensor 16(Forward Pressure Control). At this time, flow can be directed away from flow sensor 53 so that its drift correction can be determined. At some time before a sample is injected, the Split mode of operation is entered. Three way valve 51 directs gas flow through the flow sensor. Valve 55 is then controlled by flow sensor 53. At the same time, valve 57 is under the control of pressure sensor 16(Back Pressure Control). After some time is allowed for flow equilibrium to be established, injection of the sample begins. After the injection of the sample, splitless mode operation recommences. Valve 55 is again placed under pressure sensor 16's control. Valve 57 is shut and flow is directed away from flow sensor 53.

If the GC has a purge pack inlet and operates as a capillary inlet, flow control may not be required. Pressure control can be used and the flow sensor acts as an indicator. No flow sensor would be required for on-column injection.

By using a flow sensor with fast response time, the null offset of the sensor can be measured and compensated continuously during a GC run. Flow control stability is enhanced with a two cycle process. During the calibration cycle, flow is directed away from the flow sensor, the sensor output is measured and the null offset reading is used to establish a new flow base line. In a flow measurement cycle, flow is directed through the flow sensor, the flow sensor output is measured and the null offset measured previously is subtracted from it. As this can be performed several times a second, the flow sensors drift can be continually compensated. This has the incidental effect of effectively compensating for temperature effects on the GC's analysis, as the GC is being continually reset during operation.

Figure 3:
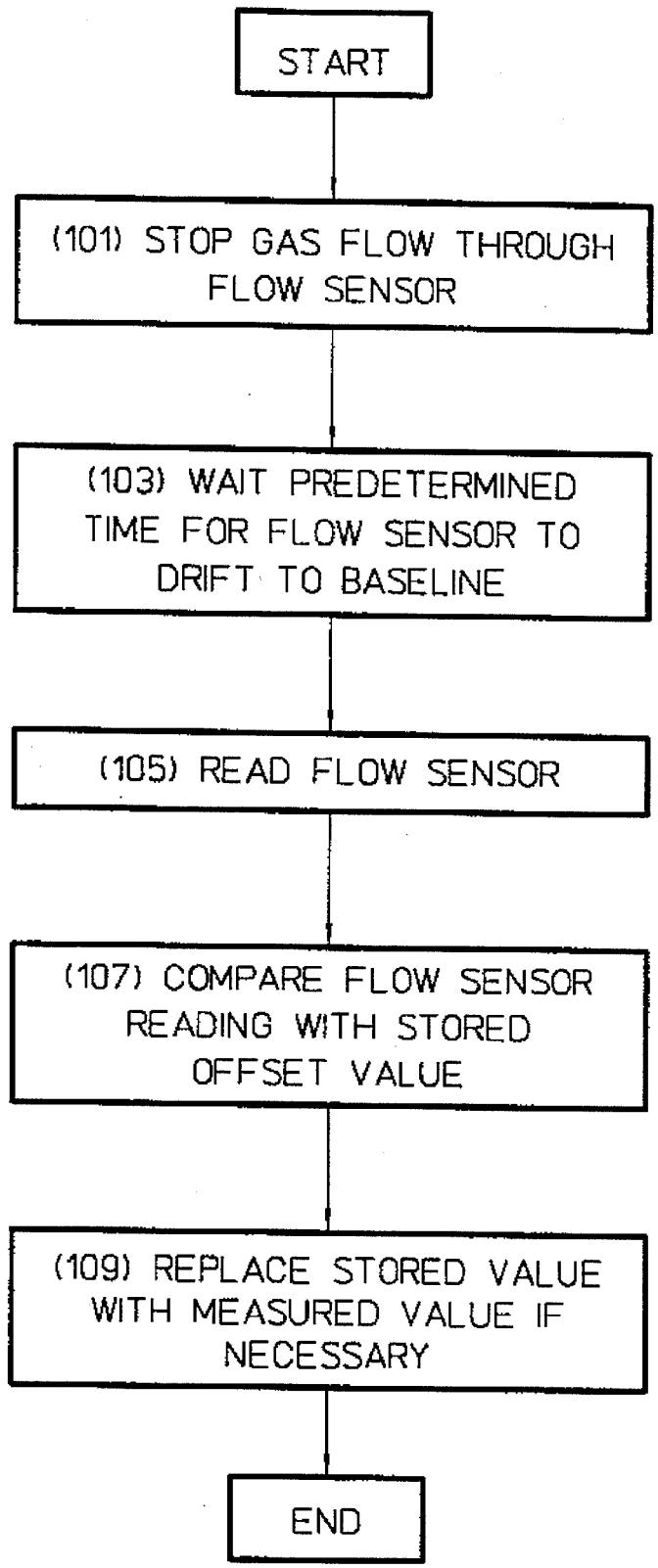
FIG. 3 is a flow chart illustrating the method of correcting the flow sensor drift.

To determine the flow sensor drift correction, the present invention begins by setting three way valve 51 so that all gas flow through flow sensor 53 is stopped(step 101, FIG. 3). After a predetermined period of time has elapsed(step 103, FIG. 3), a reading is taken from the flow sensor(step 105, FIG. 3). This reading is compared with a predetermined flow sensor offset(step 107, FIG. 3). This predetermined value may be measured at the factory or during the GC's first use. If the reading exceeds the predetermined value by a threshold amount, the new reading replaces the predetermined sensor offset and operation and analysis continues therefrom(step 109, FIG. 3). Otherwise, the predetermined value continues to be used.

Correcting the drift of the pressure sensor first requires that the pressure sensor be vented to ambient pressure. The reading of the pressure sensor at ambient air pressure is then used as the pressure sensor drift correction value as needed.

Determining the drift correction of both the flow and pressure sensor can occur at any time that the GC is not being used to analyze a sample. At the user's option, it can occur once every time the machine is turned on, once each time a sample is analyzed, or at any other rate the user desires.

What is claimed is:

1. In a gas chromatograph having at least a processor and a sample/carrier gas input section with at least a first valve controllable by and coupled to the processor and a first flow sensor, a method for correcting the drift of the flow sensor comprising the steps of:

setting the at least first valve so no carrier gas/sample flows through the flow sensor;

reading the flow registered by the flow sensor using the processor;

comparing the flow measured by the flow sensor with a reference value stored in the processor;

using the reference value in the processor if the flow registered by the flow sensor does not exceed the reference value by a first predetermined amount; and replacing the reference value with the flow registered by the flow sensor if the flow registered by the flow sensor does exceed the reference value by the first predetermined amount.

2. The method of claim 1 wherein the steps of setting the at least first valve, reading the flow registered by the flow sensor, comparing the flow measured by the flow sensor, using the reference value in the processor, and replacing the measured value in the processor are repeated during one sampling run of the gas chromatograph.

3. The method of claim 1 wherein the sample/carrier gas input section comprises a split/splitless gas input section.

4. The method of claim 1 wherein the sample/carder gas input section comprises a cool on column gas input section.

* * * * *